United States Patent [19]

Bos et al.

[11] Patent Number: 5,762,836
[45] Date of Patent: Jun. 9, 1998

[54] METHOD FOR MAKING AN INTRAOCULAR IMPLANT WITH A SOFT LENS

[75] Inventors: Gilles Bos, La Balme de Sillingy; Angel Ortuno, Choisy; Franck Villain, Annecy, all of France

[73] Assignee: W.K. & Associes, Paris, France

[21] Appl. No.: 666,403

[22] PCT Filed: Oct. 13, 1995

[86] PCT No.: PCT/FR95/01344

§ 371 Date: Jun. 11, 1996

§ 102(e) Date: Jun. 11, 1996

[87] PCT Pub. No.: WO96/11792

PCT Pub. Date: Apr. 25, 1996

[30] Foreign Application Priority Data

Oct. 14, 1994 [FR] France ................... 94 12274
Oct. 14, 1994 [FR] France ................... 94 12275

[51] Int. Cl.⁶ .................................................. B29D 11/00
[52] U.S. Cl. ...................... 264/1.7; 264/2.5; 264/2.7; 425/808; 425/812
[58] Field of Search ..................... 364/1.7, 2.7, 2.5; 425/808, 812

[56] References Cited

U.S. PATENT DOCUMENTS 4,501,715  2/1985  Barfield et al. .................. 264/248
5,074,942  12/1991  Kearns et al. .................. 156/154
5,182,053  1/1993  Creaseman et al. .................. 264/1.7
5,217,491  6/1993  Vanderbilt .................. 264/1.7

FOREIGN PATENT DOCUMENTS 0 331 457  9/1989  European Pat. Off. .
1 362 588  4/1964  France .
2 510 768  2/1983  France .
2 676 357  11/1992  France .
2 676 358  11/1992  France .
57-094706  6/1982  Japan .

OTHER PUBLICATIONS

Copy of European Search Report issued for PCT/FR95/01344.

Primary Examiner—Mathieu D. Vargot
Attorney, Agent, or Firm—Wolf, Greenfield & Sacks P.C.

[57] ABSTRACT

The invention relates to a method of making an intraocular implant having a flexible lens. The method includes in using a mold having two parts (12) and (16) which are disposed on either side of a plate (20), e.g. made of PMMA, which plate includes a central orifice. The material (32) that is to constitute the lens portion is disposed in the central cavity of the mold. This material may be an acrylic, for example. After unmolding, the plate (20) is machined to make the haptic, and optionally the part (32) is machined to make the lens.

34 Claims, 3 Drawing Sheets

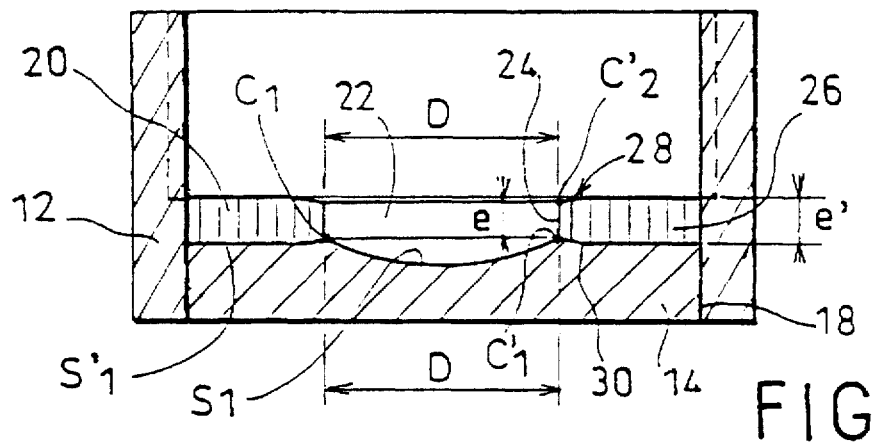
FIG_1
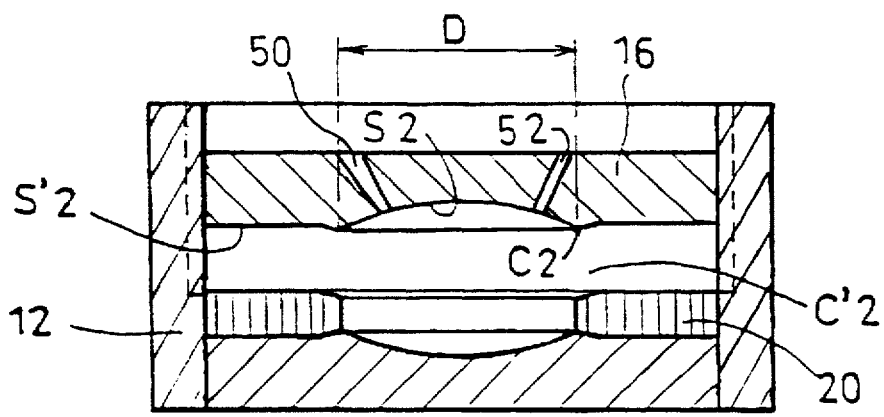
FIG_2
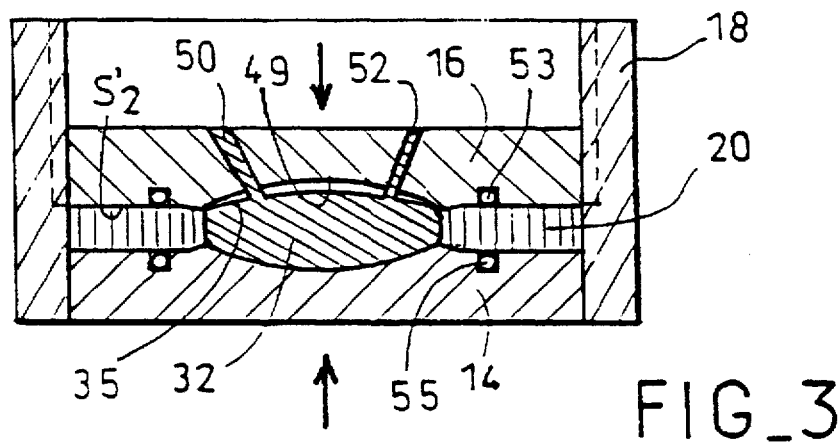
FIG_3

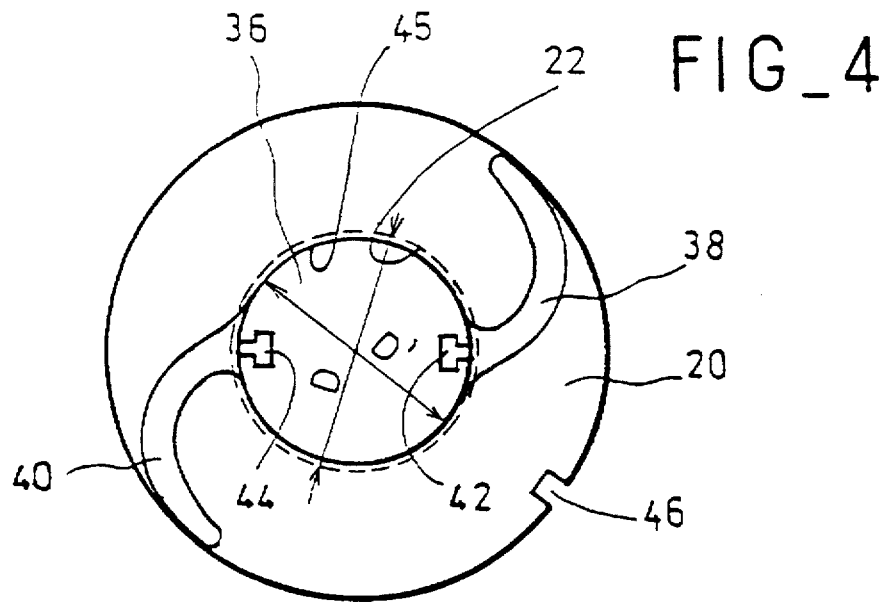
FIG_4
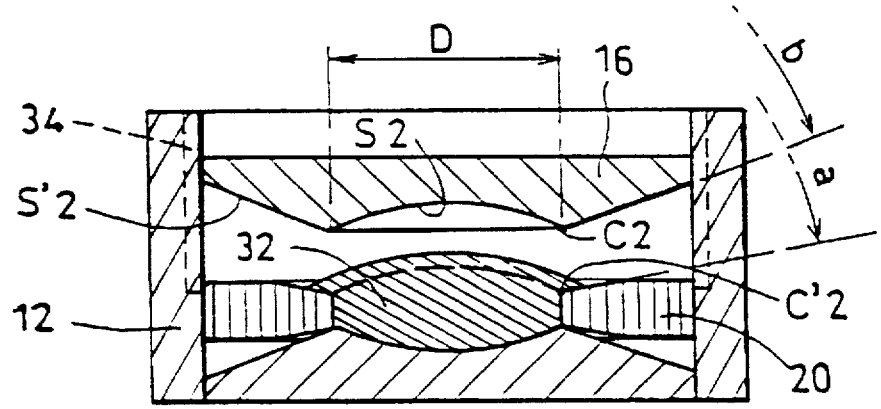
FIG_5
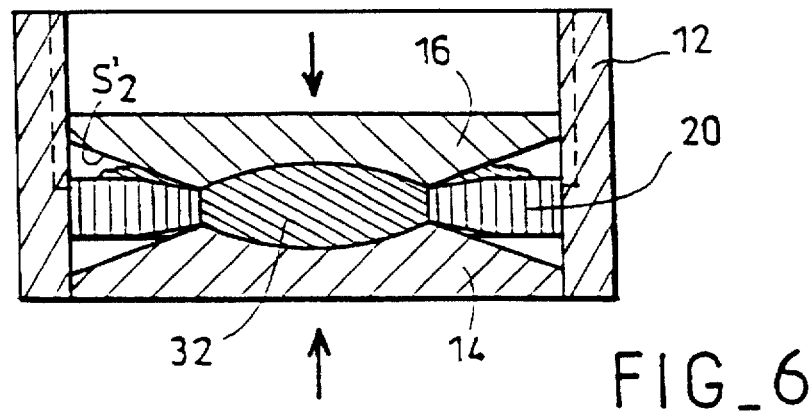
FIG_6

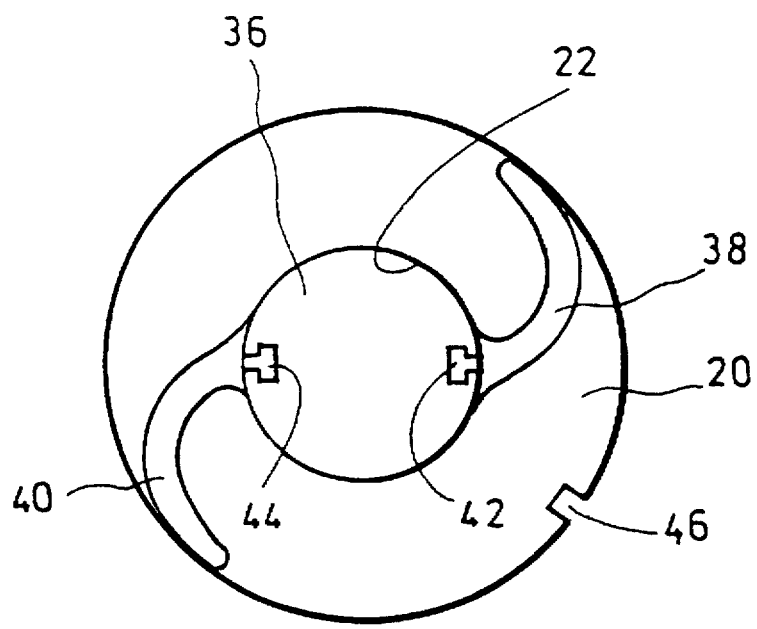
FIG_7

METHOD FOR MAKING AN INTRAOCULAR IMPLANT WITH A SOFT LENS

BACKGROUND OF THE INVENTION

1. Field of the Invention

The present invention relates to a method of making an intraocular implant including a lens that is flexible, i.e. a lens that can be folded.

2. Description of Related Art

Intraocular implants are becoming widespread. They constitute a system for correcting human eyesight which can, in some cases, replace contact lenses or external correcting eyeglasses. An intraocular implant is essentially constituted by an optical portion that is generally circularly or slightly oval in shape constituting the correcting lens system proper, and by a haptic portion which serves for installing, fixing, and holding the lens portion in the correct position inside the eye.

The most recent intraocular implants are of a monolithic PMMA structure, i.e. the lens and the haptic portion are cut out from a single block of that material. The haptic portion usually comprises two curved and flexible loop-like portions extending from opposite sides of the lens portion and being connected thereto at two points of its periphery that are substantially diametrically opposite.

To provide suitable optical correction, the lens portion must have a diameter of about 5 mm to 6 mm. Given that the material used is rigid, at least in the portion thereof constituting the lens, it is necessary to make an incision in the patient's cornea that is at least 6 mm long, and in practice longer still because of the presence of the haptic portions.

It should also be emphasized that very many implants of that type have been developed, in particular those described in French patent applications Nos. 2 676 358 and 2 676 357, with the implants differing essentially in the shape and the dimensional characteristics of the loops forming the haptic portion, which characteristics are adapted, in particular, to the requirements of practitioners who install such implants in the eyes of patients. In other words, the manufacturers of intraocular implants have now thoroughly mastered defining in particular the loops of such implants, their mechanical properties, in particular concerning bending, and the stability over time of those mechanical characteristics. The operation of removing the natural lens, which operation is usually performed immediately before installing an implant, at least a posterior chamber implant, used to require an incision of large size to be made in the cornea, so monolithic PMMA implants were very well adapted insofar as the incision necessarily made for the cataract operation was quite large enough.

Nowadays, a cataract operation is usually performed by the "phaco-emulsification" operating technique. That technique enables the opaque natural lens to be removed by inserting into the eye an ultrasound probe that is fitted with an irrigation and suction system. The combined action of ultrasound and a flow of BSS serves to remove the natural lens by emulsification.

Compared with prior techniques, that operating technique has the advantage that the instruments used for removal purposes can be inserted into the eye via an incision of small size only made in the cornea, using a knife that is precalibrated to 3.2 mm. It will thus be understood that it would be advantageous to have implants capable of being inserted into the eye via the incision made for the phaco-emulsification operation, i.e. through an incision having a length of about 3 mm or 4 mm.

It will also be understood that monolithic PMMA implants are rigid and unsuitable for that purpose. That is why development has begun on "flexible" intraocular implants which are made, at least in the lens portion thereof, out of a flexible material, thus enabling the lens portion to be folded prior to insertion into the eye through the incision, with the lens portion returning to its initial shape after being put into place in the eye. At present, two broad types of substance are used for making flexible lenses. These substances are usually referred to generically firstly as "flexible acrylics" and secondly as "polysiloxane gel". These substances have the optical properties required for making a lens system and they are also biocompatible.

When making intraocular implants having a flexible lens, one of the crucial points is making the haptic portion and in particular securing the haptic portion to the lens.

Solutions that have already been used for solving that problem include firstly a solution in which orifices are formed in the flexible lens portion when it is made, serving subsequently to receive one end of each haptic portion element and to secure it to the lens portion. Another solution consists in making the lens portion by molding after placing the elements of the haptic portion in the mold so that the ends of the haptic portions constitute the equivalent of inserts in the mold cavity.

Those various techniques suffer from the major drawback of not enabling haptic portions to be made like those to be found on monolithic PMMA implants. Usable haptic portions are made of filaments, and usually polypropylene filaments which offer a limited range of possible shapes. In addition, those haptic portions behave mechanically in ways that have been experimented with for a long time without great success. In other words, the long experience acquired in manufacturing monolithic implants having a PMMA haptic portion is no longer applicable. In addition, in the first type of method, additional manufacturing operations are required, thereby naturally increasing the cost of the implant.

To solve that problem, proposals have very recently been made to make an implant as follows. Initially a cylinder is made of diameter equal to that of the lens portion and the cylinder is made out of a first material that is flexible. Thereafter, the cylinder is placed in a mold whose cavity defines an annular space around the cylinder. An annular layer of a second material is molded onto the cylinder, which second material is preferably PMMA. The first material is selected in such a manner that, during the molding operation, the networks of the first and second materials interpenetrate, which is supposed to achieve a physico-chemical bond that is strong enough mechanically to ensure bonding between the lens portion which is subsequently machined from the cylinder and the haptic portion which is subsequently machined from the layer of PMMA surrounding the cylinder. Nevertheless, that technique suffers from the drawback of being relatively complex and of being capable of being implemented with certain types of flexible material only, typically the materials known as "hydrogels".

An object of the present invention is to provide a method of making an intraocular implant having a flexible lens which is simple to implement while making it possible to obtain a haptic portion made of PMMA or similar material that can take any desired shape, thus making it possible to benefit from past experience of monolithic intraocular implants made of PMMA or similar material.

SUMMARY OF THE INVENTION

To achieve this object, the method of making an intraocular implant comprising a lens portion defined by two surface potions and by a periphery bounded by two closed contours, each closed contour bounding one of said surfaces and made of a first material that is flexible, and a haptic portion made of a second material that is rigid compared with said first material, is characterized in that it comprises the following steps:

- a mold is provided having first and second mold parts each having an inside face defining a surface that is bounded by a closed contour;
- a plate made of a second material is provided that has a central recess whose periphery is of dimensions not less than those of the periphery of the intended lens portion;
- said plate is disposed between said first and second mold parts in such a manner that the closed contours of said mold parts face said plate, said surfaces of the mold parts being defined in such a manner that the volume bounded by said surfaces and said recess of the plate contains at least the shape of the intended lens portion;
- said mold parts are applied with pressure against said plate, with said mold parts defining in said position a volume whose shape is at least equal to that of the lens portion to be made, and a volume of said first material in liquid form is disposed in the volume bounded at least by said recess and the surface of the bottom part of the mold;
- treatment is applied to said first material so that it takes on its solid state;
- the piece obtained in this way is unmolded; and
- at least said plate is machined so as to obtain the desired shape of haptic.

In a first implementation, in which said material shrinks in volume between the liquid state and the solid state, said first material is machined to give it the desired lens shape.

It will be understood that if the method is implemented with a material that can suffer significant volume reduction during the transformation operation causing it to take up its final shape, then the definitive shape of the lens portion must be obtained by subsequent machining. For a material that shrinks, the mold cavity as defined in particular by the two mold parts is such that, even after shrinking, the mass of material that is going to constitute the lens portion is an envelope encompassing the final shape of the lens portion.

It will also be understood that the plate of second material which is preferably made of PMMA can be machined by the techniques used in the past for making monolithic intraocular implants made entirely out of a PMMA type material. In other words, the manufacturer can benefit from long experience in defining the shapes and dimensions of the haptic portions, and in particular haptic loops as made in the past.

Depending on the natures of the two materials used, the mechanical bonding may be obtained in a first case by providing extensions into the central recess of the plate, which extensions form inserts that are thus embedded in the optical portion.

In a variant embodiment, it is possible to use two materials that are selected so as to achieve interpenetration of the networks of the two materials during transformation of the first material in the mold, which interpenetration should not alter the stiffness of the first material.

There are two different ways in which the lens portion can be made by molding. In a first case, the two mold parts are applied with pressure against the plate and the material is injected in liquid form into the mold cavity. In a second case, prior to putting the top part of the mold into place, excess material is placed in the recess formed by the bottom part of the mold and the orifice in the plate of material that is to form the haptic portion, and then the top part of the mold is put into place and the two parts of the mold are pressed against the plate.

Which method is selected is a function of whether the material is initially in the liquid state or is relatively viscous.

It will also be understood, that when the first material shrinks little and is injected, then this first implementation of the method makes it possible to restrict machining operations for obtaining the final shape of the implant to eliminating traces of injection from the lens portion and to machining the plate of the second material which is preferably made of PMMA, which technique is thoroughly mastered by the manufacturers of intraocular implants.

In a second implementation, the method is characterized in that it comprises the following steps:

- a bottom mold part is provided having a top surface with a central portion corresponding to said first portion of surface bounded by said first closed contour and whose peripheral portion is set back relative to said first contour;
- a plate is provided that is made of said second material and that has a central recess whose periphery is bounded by said first and second closed contours;
- said plate is disposed facing said bottom part of the mold in such a manner that said closed contour of said first portion faces the first closed contour of said plate;
- a second mold part is disposed above said plate, said second mold portion having a bottom surface whose central portion corresponds to said second surface portion bounded by said second closed contour and whose peripheral portion is set back from said second closed contour, in such a manner that the second closed contours of said plate and of the bottom surface of said second mold part face each other;
- a volume of the first material in liquid form is inserted into the space defined by at least one of said surfaces and by said recess, said volume being not less than the volume of said lens portion;
- the said mold parts are applied with pressure against said plate in such a manner that said first and second closed contours come respectively into mutual contact whereby said first material fills all of the volume bounded by said recess and said surface portions, any excess of said first material being expelled from said volume;
- said first material is subjected to treatment to cause it to set and to bring it to its final state;
- the piece obtained in this way is unmolded; and
- said plate is machined to achieve the desired shape for the haptic portion.

It will be understood that this second implementation of the method takes place with a material that does not reduce significantly in volume during the transformation operation taking it from its transformation shape to its final shape.

It would also be understood that the final shape of the lens portion is directly defined by the shape of the two mold parts. It will also be understood that the plate of the second material which could preferably be PMMA can be machined using the techniques used in the past for making monolithic intraocular implants out of a PMMA type material. In other words, the manufacturer can benefit from long experience in defining the shapes and sizes of haptic portions, and in particular haptic loops, as made in the past.

Depending on the natures of the two materials used, mechanical bonding may be obtained in a first case by providing extensions into the central recess of the plate, which extensions form inserts that are thus embedded in the lens portion.

In a variant embodiment, it is possible to use two materials that are selected so as to achieve a bonding of interpenetration of the networks of these two materials during transformation of the first material in the mold, which interpenetration should not alter the stiffness of the first material.

In another variant implementation, the periphery of the central recess of the plate can be prepared to achieve adhesion between the first and second materials during the molding operation. These three implementations can be associated in pairs, or all three used together.

It will also be understood that this second implementation of the method makes it possible to limit machining operations for obtaining the final shape of the implant to machining the plate of second material which is preferably PMMA, which technique is thoroughly mastered by the manufacturers of intraocular implants.

BRIEF DESCRIPTION OF THE DRAWINGS

Other characteristics and advantages of the present invention appear better on reading the following description of various implementations of the invention given as non-limiting examples. The description refers to the accompanying figures, in which:

FIG. 1 is a vertical section view through a mold in its first position while making an implant in application of a first implementation;

FIG. 2 is a similar view showing the installation of the second mold part;

FIG. 3 shows the mold in its closed position;

FIG. 4 shows the product obtained at the end of the molding step and shows part of the operation of machining the haptic portion;

FIGS. 5 and 6 are a vertical section through a variant embodiment of the mold for implementing the method in a variant of the first implementation and in a second implementation; FIG. 7 shows the product obtained at the end of the molding step and shows part of the operation machining the haptic portion in the second implementation.

DETAILED DESCRIPTION

Before describing in detail preferred implementations of the method of the invention for manufacturing an intraocular implant, the principle thereof is described.

In a first implementation of the invention, the principle of the method consists in providing a plate of a second material that is to constitute the haptic portion, and which material is PMMA, for example. The plate includes a central recess whose periphery is at least of the dimensions of the periphery of the lens portion. In other words, the periphery of the lens portion to be made must be contained in the central recess of the plate, for reasons that are explained below. The dimensions of the plate are sufficient to enable the entire haptic portion to be machined therefrom using techniques that are themselves known. The plate is disposed between the two parts of a mold which define, in particular, envelope surfaces of the two surfaces bounding the lens portion. A first material in liquid form is inserted into the cavity constituted by the recess in the plate and the two mold parts, which material has the necessary optical properties and is capable of being transformed to reach a solid final state. The material may exhibit a phenomenon of shrinking during this transformation. After performing the transformation on the material and unmolding the resulting product, it suffices to machine the plate so that all that remains thereof is the desired haptic portion and to machine the material that is to constitute the lens portion so as to give it the desired shape. Typically, in the case considered most particularly, there are two identical loops, and both loops can be machined in exactly the same manner as is used for making monolithic intraocular implants out of PMMA.

With reference now to FIGS. 1 to 4, details of a first implementation of the method of the invention for manufacturing an intraocular implant are described.

As already mentioned, the intraocular implant is essentially made by a molding operation. The mold is essentially constituted by a cylindrical annular ring 12, by a bottom part 14, and by a top part 16. The bottom part 14 has a central portion whose top face is bounded by a surface portion S1 which is an envelope of one of the optical faces of the implant to be made. Surface portion S1 is bounded by a closed contour C1. Beyond the closed contour C1, the bottom part 14 of the mold includes a peripheral portion whose top face is defined, for example, by a portion of a cone or a frustoconical surface S'1 which may be set back relative to the contour C1 or may be plane. As shown in the figure, the outer periphery 18 of mold part 14 has the same diameter as the inside face of the cylindrical ring 12.

According to the invention, to make an implant, a plate 20 is placed inside the ring 12 between the bottom part 14 and the top part 16, which plate is made of a material that is suitable for forming the haptic portion of the implant. Typically, for the reasons given above, the material is preferably PMMA. Nevertheless, other types of material could be used. The outer contour of the plate 20 has the same diameter as the inside diameter of the ring 12. The plate 20 has a central orifice 22 whose diameter D is not less than the diameter of the lens portion to be made. The orifice 22 is thus surrounded by a periphery 24, said periphery being itself bounded by a lower, first closed contour C'1 and by an upper, second closed contour C'2. In the particular case shown in the figure, these contours are circular, of diameter not less than D, and they are disposed in parallel planes. To make other types of lens, different dispositions could be used. Also, it should be observed that the lower contour C'1 of the plate 20 preferably coincides exactly with the closed contour C1 of the bottom part of the mold 14. The periphery 24 of the orifice 22 is of thickness e which is not less than the thickness of the contour of the lens portion to be made. The main portion of the plate 20, given reference 26, has a thickness e' significantly greater than the thickness e of the wall 24. This thickness e' is sufficient to enable the haptic portions to be cut out therefrom subsequently. It is usual for the haptic portions or haptic loops to be at a certain angle relative to the plane of the lens of the implant. It is also preferable for the periphery 24 of the orifice 22 to be connected to the main portion 26 of the plate via two surfaces 28 and 30 which may be plane.

In the following step, shown in FIG. 2, the second part 16 of the mold is placed inside the cylindrical ring 12. This part 16 has a bottom face with a central portion that defines a surface S2 bounded by a closed contour C2. The surface S2 is an envelope of the second face of the lens portion to be made and the contour C2 preferably coincides with the upper, second contour C'2 of the plate. The portion 16 of the mold also includes a peripheral zone which is preferably bounded by a conical or frustoconical surface S'2. In addition, the top part 16 includes at least one injection orifice 50 and at least one vent 52. The injection orifice(s) and the vent(s) could equally well be disposed in the bottom part of the mold or in the plate.

The top part of the mold 16 is then lowered so that its closed contour C2 comes face to face with the contour C'2 of the plate, and pressure is applied to the mold parts 14 and 16 so that the internal cavity 49 bounded by the surfaces Si and S2 and by the periphery 24 of the orifice 22 in the plate 20 is sealed. To further improve sealing, it is possible to interpose two annular sealing rings between the plate 20 and the mold parts 14 and 16. This is shown at 53 and 55 in FIG. 3.

The material 32 for constituting the lens portion is then injected into the cavity 49 through the orifice 50. This material is in liquid form. In a preferred example, the material is a hydrogel which, in this stage, is in the form of a liquid solution of monomers. It is known that such a material is subject to non-negligible shrinkage during transformation or "setting" on passing from the liquid state to the solid state. The material is subjected to appropriate treatment to cause it to solidify. It will be understood that the ring 12 serves solely for relative positioning and guidance of the two mold parts so that the closed contours C1, C2, C'1, and C'2 do indeed come face to face. The ring performs no sealing function. Sealing of the mold cavity is achieved by contact with pressure between the closed contours. As already mentioned, sealing may be improved by sealing rings. Depending on the nature of the material used, the treatment may consist in heat treatment or bombardment by means of photons or particles such as electrons. For the material under consideration in this example, this gives rise to shrinkage. This is shown at 35 in FIG. 3.

When this treatment has been finished, it suffices to unmold the resulting part. This is shown in FIG. 4. The resulting part thus comprises the plate 22 and the lens zone 36 which is constituted by the material 32.

To ensure mechanical bonding between the periphery of the lens 36 and the periphery of the orifice 22 in the plate 20, i.e. between the haptic portion and the lens portion, various techniques can be envisaged depending on the natures of the materials used. It is possible to select materials which, during transformation of the first material that is to constitute the lens, are such as to present a phenomenon of bonding of interpenetration between the two materials. If the plate 20 is made of PMMA, then the first material may be pHEMA. Such interpenetration is usually accompanied by stiffening of the periphery of the lens portion 36.

Another solution or a complementary solution consists in providing two extensions of the plate such as 42 and 44 extending inside the orifice 22 in the plate 20, which extensions act as inserts while the lens portion is being made by molding. To finish off the piece, it is necessary to machine both the plate 20 and the block of material that is to constitute the lens portion. The machining consists firstly in giving the lens portion 36 the required shape by machining its two surfaces S1 and S2. It also consists in machining the plate 20 so as to define loops 38 and 40 in the particular example described. When the networks of the two materials interpenetrate, the machine also includes a step of cutting out the periphery of the lens portion 36 along a line 45 so as to remove the interpenetration zone which may be stiff. This cut is performed at a diameter D' equal to the diameter of the lens to be made. That is why the diameter D of the central recess 22 in the plate is greater than the diameter of the lens portion.

A third solution or complementary solution consists in preparing the surface of the orifice 22 or of the extensions 42 and 44 so as to obtain adhesion between the two materials.

It should be added that even if the first material presents negligible shrinkage, and if there is no reaction between the two materials, it can still be advantageous to machine the material constituting the lens, e.g. to eliminate traces of injection.

In any event, an intraocular implant is obtained comprising:

firstly, loops cut out from the portion 20, which is typically made of PMMA; and secondly, a lens machined in the material 32 that is injected into the mold.

The lens is flexible either because the selected material is hydrophilic, in which case hydration thereof acts as a plasticizer; or else because the selected material has a glass-transition temperature that is lower than ambient temperature, in which case it must be machined below said temperature.

FIGS. 5 and 6 show a variant mold for making an intraocular implant, this variant concerning the way in which the material is disposed in the mold cavity, with insertion no longer being performed by injection.

In this variant of the first implementation, the bottom part 14 of the mold and the annular ring 12 are identical to those shown in FIG. 1. There is therefore no need to describe them again.

In the following step, as shown in FIG. 5, a volume 32 of material that is to constitute the lens has just been deposited in the cavity constituted by the surface S1 of the bottom part 14 of the mold and by the orifice 22 in the plate 20. In a preferred example, this material may typically be an acrylic which, at this stage, is in the form of a liquid solution of monomers. The solution may have been pre-polymerized in order to obtain a syrup having viscosity compatible with depositing a drop 32 of the substance. This material is known to present non-negligible shrinkage on transformation or "setting" when it passes from the liquid state to the solid state. The deposited volume 32 is significantly greater than the volume of the lens to be made. The second part 16 of the mold is then placed inside the cylindrical ring 12. This part 16 has a bottom face which includes a central portion defining a surface S2 bounded by a closed contour C2. The surface S2 is an envelope of the second face of the lens portion to be made and the contour C2 preferably coincides with the upper, second contour C'2 of the plate. The mold part 16 also includes a peripheral zone which is preferably bounded by a conical or frustoconical surface S'2.

The top part 16 of the mold is then lowered so that its closed contour C2 comes up against the contour C'2 of the plate. During this operation, excess material 32 is expelled into the residual annular volume extending between the plate and the conical surface S'2 of the top part 16 of the mold. Lowering is performed in such a manner as to avoid leaving any air bubbles in the material. To facilitate exit of excess material 32, the angle at the apex a of the frustoconical portion 28 of the plate is greater than the angle at the apex b of the frustoconical surface S'2 of the top part 16 of the mold. Optionally, provision may be made in the cylindrical ring 12, and more precisely in its inside face, for vertical channels such as 34 for exhausting air. The stack constituted by the bottom part 14, the plate 20, and the top part 16 is kept under pressure in the mold. It will be understood that the ring 20 serves solely for relative guidance and positioning of the two mold parts so as to ensure that the closed contours C1, C2, C'1, and C'2 effectively coincide. The ring performs no sealing function. The mold cavity is sealed by contact with pressure between the closed contours. In addition, since the area of contact is very small, the molded piece does not include unwanted portions in the two join planes. The entire mold assembly is then subjected to treatment for causing the material 32 to be transformed from its initially liquid state to a final state that is stable at ambient temperature. Depending on the nature of the material used, the treatment may consist in heat treatment or in bombardment by means of photons or particles such as electrons. When using the material considered in the present example, shrinkage takes place. This is represented at 35 in FIG. 6.

When treatment has been finished, it suffices to unmold the piece obtained in this way. This is shown in FIG. 4. The resulting piece is thus constituted by the plate 22 and by the lens zone 36 constituted by the material 32. The lens portion is then machined as is the haptic portion, as described above. This solution is advantageous only when the material used for making the lens portion has a certain amount of viscosity in its initial state. This condition is satisfied by polysiloxane gels. With acrylics, polymerization of the substance can be started in order to bring it to the required viscous state.

When the injected material presents a large amount of shrinkage, e.g. as applies to an acrylic, the machining that needs to be performed subsequently is identical to that described with reference to FIG. 4.

With a material that presents negligible shrinkage, it is possible to give the two parts 14 and 16 of the mold the exact shape of the lens to be made and to restrict the join planes of the mold to limited surface contact areas corresponding to the closed contours C1, C2, C'1, and C'2, thereby obtaining the lens portion directly by injection molding. Machining of the lens portion is then restricted to removing traces of the injection point(s) and of the vent(s) from the surface of the piece. Naturally, the material must also be machinable at ambient temperature or at a temperature close to ambient, which does not apply to silicone gels.

In the example described in greater detail, the lens to be made is bounded by the surfaces S1 and S2 which are portions of spherical caps so as to define a lens shape. Consequently, the closed contours C1, C2, C'1, and C'2 are circular. Naturally, the surfaces S1 and S2 may be arbitrary, in particular they may be concave or convex, and they can have any desired radius of curvature. It is also clear that one of the surfaces S1 could, in fact, be plane. It is also clear, when it is desired to make an implant of the multifocal type, for example, that the surfaces S1 and S2 could be more complex. It will be understood that the shapes of the surfaces S1 and S2 do not modify the various steps of the method in any way.

When the material used presents non-negligible shrinkage, it is necessary to machine the lens portion. The shape of the cavity in the mold, and the size of the contact areas between the two mold parts and the plate are therefore not critical.

When significant material shrinkage is accepted and a network interpenetration effect is expected between the materials constituting the lens portion and the haptic portion, it is advantageous to use materials commonly named using the terms pHEMA, hydrogel, or any other flexible acrylic copolymer, with the plate 20 being made of PMMA.

Documents EP-A-0 485 197 and EP-A-0 514 096 describe flexible acrylics usable for implementing the invention. Documents U.S. Pat. No. 4 997 442, U.S. Pat. No. 5 133 745, WO-A-90/09768, and EP-A-0 492 126 describe hydrogels that can also be used for implementing the invention.

The principle of the method of the invention consists in providing a plate of a second material for constituting the haptic portion, which material is PMMA, for example. This plate includes a central recess whose periphery has exactly the same shape as the periphery of the lens portion. The dimensions of the plate are large enough to enable the entire haptic portion to be machined using techniques that are themselves known. The plate is disposed between the two parts of a mold which define, in particular, two surfaces in turn bounding the lens portion. A first material in liquid form is inserted in the cavity constituted by the recess in the plate and the two mold parts, which material has the required optical properties and is capable of being transformed so as to achieve a final state that is solid. Said material needs to present shrinkage during said transformation that is substantially negligible. After the material has been transformed and the resulting product has been unmolded, it then suffices to machine the plate in order to leave only the desired haptic portion thereof.

This second implementation of the method uses a mold identical to that described with reference to FIGS. 1, 4, and 5, so it is not described in greater detail.

In the second implementation of the method, in order to make an implant, a plate 20 is placed inside the ring 12 and above the first part 14, which plate is made of a material suitable for forming the haptic portion of the implant. Typically, for reasons mentioned above, said material is preferably PMMA. Nevertheless, it will be possible to use other types of material. The outer contour of the plate 20 has the same diameter as the inside diameter of the ring 12. The plate 20 includes a central orifice 22 whose diameter D is equal to the diameter of the lens portion that is to be made. The orifice 22 is therefore surrounded by a periphery 24, said periphery itself being bounded by a lower, first closed contour C'1 and by an upper, second closed contour C'2. In the particular example shown, the contours are circular, of diameter D, and they are disposed in parallel planes. To make other types of lens, it would be possible to use different dispositions. In addition, it should be observed that the lower contour C'1 of the plate 20 coincides exactly with the closed contour C1 of the bottom part of the mold 14. The periphery 24 of the orifice 22 has a thickness e which is exactly equal to the thickness of the contour of the lens portion to be made. The main portion of the plate 20, given reference 26, has a thickness e' that is significantly greater than the thickness e of the wall 20. This thickness e' is sufficient to enable the haptic portions to be cut out therefrom subsequently. It is known that the haptic portions or haptic loops are usually at a certain angle relative to the plane of the lens portion of the implant. It is also preferable for the periphery 24 of the orifice 22 to be connected to the main portion 26 of the plate via two surfaces 28 and 30 which, in the figure, are in the form of truncated cones, but which, more generally, depending on the particular shapes to be made, could be conical surface portions.

In the following step, shown in FIG. 5, a volume 32 of material for making the lens has just been deposited in the cavity constituted by the surface S1 of the bottom part 14 of the mold and by the orifice 22 in the plate 20. Typically, this material may be a silicone gel, which, at this stage, is in liquid form. The deposited volume 32 is greater than the volume of the lens to be made. Thereafter, the second mold part 16 is placed inside the cylindrical ring 12. This mold part 16 has a bottom face with a central portion that defines a surface S2 itself bounded by a closed contour C2. The surface S2 is identical to the second face of the lens portion that is to be made and the contour C2 coincides with the upper, second contour C'2 of the plate. The mold part 16 also includes a peripheral zone which is preferably bounded by a conical or frustoconical surface S'2.

The top mold part 16 is then lowered in such a manner that its closed contour C2 coincides exactly with the contour C'2 of the plate. During this operation, excess material 32 is expelled into the residual annular volume that extends between the plate and the conical surface S'2 of the top part 16 of the mold. Lowering is performed in such a manner as to ensure that no air bubble remains within the material. In order to facilitate removal of excess material 32, the angle at the apex a of the frustoconical portion 28 of the plate is greater than the angle at the apex b of the frustoconical surface S'2 of the top part 16 of the mold. Optionally, provision may be made in the cylindrical ring 12 and more precisely in the inside face thereof for vertical channels such as 34 for evacuating air. In the mold, the stack constituted by the bottom part 14, the plate 20, and the top part 16 is maintained under pressure. It will be understood that the ring 12 serves solely for relative guidance and positioning of the two mold parts so that the closed contours C1, C2, C'1, and C'2 do indeed face one another. The ring has no sealing function. The mold cavity is sealed by contact under pressure between the closed contours. In addition, the contact area is very small, thereby preventing unwanted parts appearing on the molded piece in the two join planes. The entire mold is then subjected to treatment to cause the material 32 to be transformed from its initial liquid state to a final state that is stable at ambient temperature. It may be considered as being a gel and thus flexible because its own glass-transition temperature is lower than ambient temperature, or else it may be hydrophilic and thus become flexible after absorbing water which acts as a plasticizer. Depending on the kind of material used, the treatment may consist in heat treatment or in bombardment by means of photons or particles such as electrons.

Once the treatment has been finished, it suffices to unmold the resulting piece. This is shown in FIG. 7. The resulting piece is then constituted by a plate 22 and by the lens zone 36 made of the material 32. To finish manufacture of the intraocular implant, it then suffices to use conventional machining techniques to cut the desired haptic portion out from the plate 22. In the example shown in FIG. 7, said haptic portion comprises two diametrically opposite loops 38 and 40 that are identical.

In order to provide mechanical bonding between the periphery of the lens 36 and the periphery of the orifice 22 in the plate 20, i.e. between the haptic portion and the lens portion, various techniques can be envisaged depending on the kinds of materials used. It is possible to select materials which, during transformation of the first material that is to become the lens, implement a network interpenetration phenomenon between the two materials. Nevertheless, it is important that this interpenetration phenomenon is not accompanied by stiffening of the periphery of the lens portion 36.

Another solution consists in providing two extensions of the plate such as 42 and 44 extending into the orifice 22 of the plate 20, which extensions subsequently act as inserts when the lens portion is made by molding. Elsewhere, there is no mechanical bonding between the two materials, i.e. between the plate and the lens portion 36. While the loops 38 and 40 are being cut out, it is naturally necessary for the portions of said loops in contact with the periphery of the lens portion to include the extensions 42 and 44. To satisfy this condition, it suffices to provide an indexing element 46 in the periphery of the plate 20 so as to enable the machining tools to be positioned angularly relative to the loops 38 and 40.

A third solution consists in initially preparing the periphery 24 of the orifice 22 in the plate so as to achieve adhesion between the material constituting the haptic portion and the material constituting the lens 36. In all cases, after the plate 20 has been cut out and machined to provide the loops, an intraocular implant is obtained which includes a lens portion 36 made of a material that is flexible and a haptic portion constituted by the loops 38 and 40, for example, and presenting exactly the same mechanical properties and exactly the same shapes as the loops of prior art monolithic intraocular implants, e.g. made of PMMA. Surface preparation may be performed on the extensions 38 and 40 that are to serve as inserts so as to improve the bonding between the two materials.

In the example described in greater detail, the lens to be made is bounded by the surfaces S1 and S2 which are portions of spherical caps serving to define a lens. Consequently, the closed contours C1, C2, C'1, and C'2 are circular. Naturally, the surfaces S1 and S2 could be arbitrary in shape, in particular they could be concave or convex, and they could have any desired radius of curvature. Also, one of the surfaces S1 could equally well be plane. It is also clear that when it is desired to make an implant, e.g. of the multifocal type, the surfaces S1 and S2 could be more complex. It will be understood that the shapes of the surfaces S1 and S2 do not alter in any way the various steps of the method.

The material used for the ring 20 is preferably PMMA.

Preferably, the material used for making the lens portion in this second implementation of the method is a silicone gel having all of the required properties, and in particular presenting very small shrinkage during transformation. Silicone gels polymerize with negligible change of volume. Silicone gels obtained by cross-linking polydimethylsiloxanes, polymethylphenylsiloxanes, polydiphenylsiloxanes, and copolymers thereof are suitable (the presence of phenyl functions serves to increase the refractive index of the material). Copolymers of silicone with acrylics, for example, are suitable.

Polysiloxanes suitable for implementing the invention are described, in particular, in the following documents: EP-A-0 226 400, EP-A-0 556 040, WO-A-93/16660, and FR-A-2 587 896.

Document EP-A-0 335 312 describes a formulation comprising polysiloxane with vinyl terminations and phenyl groups for increasing the refractive index, and a polysiloxane having hydride functions together with a UV absorber which is merely dispersed within the silicone. Apart from the dispersed UV filter, it is the same type of formulation as is used in manufacturing all silicone intraocular implants. It is preferable to use a UV filter associated in covalent manner with silicone.

It is also possible to use thermoplastic materials presenting very small shrinkage and having the required optical and biocompatible properties. Such materials have the advantage of being suitable for being injected into the mold cavity.

Finally, it is possible to use pre-polymerized acrylic resins in order to obtain a syrup of sufficient viscosity and of small shrinkage during final polymerization. The acrylic polymers concerned belong either to the family of hydrogels, or else have a glass-transition temperature (Tv) that is lower than ambient temperature. In all cases, a UV filter is added into the polymer before cross-linking. It is preferable to use a UV filter that is covalently bonded to the polymer.

It should be emphasized that when the material constituting the lens is a silicone gel, the second implementation of the method is particularly advantageous. This material cannot be machined at ambient temperature or even at a temperature close to ambient.

In addition, for the bond between the lens portion and the haptic portion, it appears to be advantageous to provide the extensions 40 and 42 on the plate 20, optionally in combination with other methods of bonding. In the final product, these extensions provide mechanical anchoring that is highly reliable for the ends of the haptic loops in the lens portion.

What we claim is:

1. A method of making an intraocular implant comprising a lens portion and a haptic portion each having a desired shape, said lens portion being bounded by first and second surfaces and by a periphery bounded by first and second closed contours, each of said contours defining one of said first and second surfaces, said lens portion being made of a flexible first material, said haptic portion being made of a second material that is rigid relative to said first material, the method comprising steps of:

providing a mold having first and second mold parts each having an inside face defining a surface that is bounded by a closed contour;

providing a plate made of said second material that has a central recess with a periphery having dimensions greater than or optionally equal to dimensions of the periphery of said lens portion;

disposing said plate between said first and second mold parts in such a manner that the closed contours of said mold parts face said plate, said surfaces of said mold parts being bounded in such a manner that a volume bounded by said surfaces of said mold parts and said recess of said plate has at least the shape of said lens portion;

applying said mold parts with pressure against said plate, said mold parts defining a cavity having a volume with a shape that approximates the desired shape of said lens portion to be made;

disposing a volume of said first material in liquid form in the volume of said cavity bounded at least by said recess and said surface of one of said mold parts;

solidifying said first material into a shape that approximates the desired shape of said lens portion;

unmolding said plate and said first material; and machining said plate and said first material so as to obtain the desired shapes of said haptic portion and said lens portion.

2. A method according to claim 1, wherein at least one of said first and second mold parts and/or said plate includes at least one injection orifice, said mold parts being applied with pressure against said plate in such a manner to form a sealed cavity, said first material being injected in liquid form into said cavity through said injection orifice.

3. A method according to claim 1, wherein at least one of said first and second mold parts and/or said plate includes at least one vent.

4. A method according to claim 1, wherein said first material decreases in volume on transforming from the liquid state to the solid state, and said surfaces of said first and second mold parts are envelopes of the first and second surfaces that define said lens portion.

5. A method according to claim 1, wherein machining said first material includes machining said first and second surfaces that define said lens portion.

6. A method according to claim 1, wherein said first material cooperates with said second material to form a bond by network interpenetration at an interface therebetween, and the dimensions of the periphery of said recess in said plate are not less than the dimensions of said lens portion.

7. A method according to claim 6 wherein machining said first material includes eliminating from the periphery of said first material an annular zone in which network interpenetration has taken place between said first and second materials, with the exception of zones where said haptic portions are coupled to the periphery of said lens portion.

8. A method according to claim 1, wherein said first material presents a negligible decrease in volume on being transformed from the liquid state to the solid state, said surfaces of said first and second mold parts being identical to the first and second surfaces defining said lens portion, the periphery of the recess in said plate being identical to the periphery of said lens portion.

9. A method according to claim 8, wherein machining said first material includes at least in removing an injection point of said first material into said cavity, and a vent.

10. A method according to claim 1, wherein said second material is PMMA and said first material is a hydrophilic acrylic compound.

11. A method according to claim 1, wherein said second material is PMMA and said first material is an acrylic compound having a glass-transition temperature below ambient temperature.

12. A method according to claim 1, wherein said first material is disposed in said cavity prior to said mold parts being applied against said plate, the volume of said first material being greater than the volume of said cavity that results from applying said mold parts against said plate.

13. A method according to claim 12, wherein said plate has at least one anchoring portion projecting into said recess, whereby said anchoring portion forms an insert inside said lens portion after said first material has solidified.

14. A method according to claim 12, wherein said first and second materials are selected to enable network interpenetration to take place between said first and second materials during solidification of said first material, thereby securing the periphery of said recess in said plate to the periphery of said lens portion.

15. A method according to claim 13, wherein said first and second materials are selected to provide network interpenetration between said first and second materials during solidification of said first material, thereby securing the periphery of said recess in said plate to the periphery of said lens portion, and said anchor portion in said first material.

16. A method according to claim 1, further including a step of preparing the periphery of said recess in said plate to provide adhesion between said first and second materials.

17. A method according to claim 13, wherein said anchor portion is prepared to provide adhesion between said first and second materials.

18. A method for making an intraocular implant comprising a lens portion and a haptic portion each having a desired shape, said lens portion having a volume and being defined by first and second surface portions and by a periphery bounded by first and second closed contours, each closed contour itself bounding one of said surface portions, said lens portion being made of a flexible first material and said haptic portion being made of a second material that is rigid relative to said first material, the method comprising steps of:

providing a bottom mold part having a top surface with a central portion corresponding to said first surface portion bounded by said first closed contour and having a peripheral portion that is set back relative to said first closed contour;

providing a plate that is made of said second material and that has a central recess with a periphery that is bounded by said first and second closed contours;

disposing said plate facing said bottom mold part in such a manner that said first closed contour of said first surface portion faces the first closed contour of said plate;

disposing a second mold part above said plate, said second mold portion having a bottom surface with a central portion that corresponds to said second surface portion bounded by said second closed contour and having a peripheral portion that is set back from said second closed contour, in such a manner that the second closed contours of said plate and of the bottom surface of said second mold part face each other;

inserting a volume of said first material in liquid form into a space defined by at least one of said surface portions and by said recess, said volume of said first material being not less than the volume of said lens portion;

applying said mold parts with pressure on either side of said plate in such a manner that said first and second closed contours come respectively into mutual contact and said first material fills all of a cavity bounded by said recess and said surface portions, said cavity corresponding to the desired shape of said lens portion, any excess of said first material being expelled from said cavity;

solidifying said first material to bring said first material to a stable final state having a shape corresponding to the desired shape of said lens portion;

unmolding said plate and said first material; and machining said plate to achieve the desired shape for said haptic portion.

19. A method according to claim 1, wherein said plate has at least one anchor portion projecting into said recess, whereby said anchor portion forms an insert inside said lens portion after said first material has been solidified.

20. A method according to claim 18, wherein said first and second materials are selected so as to form a bond by network interpenetration between said first and second materials during solidification of said first material, thereby securing the periphery of said recess of said plate to the periphery of said lens portion.

21. A method according to claim 19, wherein said first and second materials are selected so as to achieve network interpenetration between said first and second materials during solidification of said first material, thereby securing the periphery of said recess of said plate to the periphery of said lens portion, and said anchor portion in said first material.

22. A method according to claim 18, further comprising a step of preparing the periphery of said recess of said plate to provide adhesion between said first and second materials.

23. A method according to claim 19, wherein said anchor portion is prepared to provide adhesion between said first and second materials.

24. A method according to claim 18, wherein said second material is PMMA.

25. A method according to claim 18, wherein said first material is a polysiloxane.

26. A method according to claim 18, wherein said first material is a thermoplastic material.

27. A method according to claim 18, wherein said first material is an acrylic polymer from the hydrogel family.

28. A method according to claim 18, wherein said first material is an acrylic polymer having a glass-transition temperature lower than ambient temperature.

29. A method according to claim 25, wherein said second material comprises an anti-UV filtering agent that is covalently bonded.

30. A method according to claim 18, wherein said first and second surface portions are spherical caps, and said first and second closed contours are two equal and mutually parallel circles.

31. A method according to claim 30, wherein said plate has a main portion with a first thickness and the periphery of said recess has a second thickness that is less than the first thickness, said main portion being connected to the periphery of said recess via at least one coupling conical surface portion having a first angle.

32. A method according to claim 31, wherein the peripheral portion of at least one of said bottom and top mold parts facing the face of said plate which has said coupling conical surface portion includes, beyond said circular closed contour, a conical surface portion having a second angle that is smaller than the first angle.

33. A method of making an intraocular implant comprising a lens portion and a haptic portion each having a desired shape, said lens portion being bounded by first and second surfaces and by a periphery bounded by first and second closed contours, each of said contours defining one of said first and second surfaces, said lens portion being made of a flexible first material, said haptic portion being made of a second material that is rigid relative to said first material, the method comprising steps of:

providing a mold having first and second mold parts each having an inside face defining a surface that is bounded by a closed contour;

providing a plate made of said second material that has a central recess with a periphery having dimensions greater than or optionally equal to dimensions of the periphery of said lens portion, said plate having at least one anchoring portion projecting into said recess;

disposing said plate between said first and second mold parts in such a manner that the closed contours of said mold parts face said plate, said surfaces of said mold parts being bounded in such a manner that a volume bounded by said surfaces of said mold parts and said recess of said plate has at least the shape of said lens portion;

applying said mold parts with pressure against said plate, said mold parts defining a cavity having a volume with a shape that approximates the desired shape of said lens portion to be made;

disposing a volume of said first material in liquid form in the volume of said cavity bounded at least by said recess and said surface of one of said mold parts;

solidifying said first material into a shape that approximates the desired shape of said lens portion with said anchoring portion forming an insert inside said lens portion;

unmolding said plate and said first material; and machining said plate and said first material so as to obtain the desired shapes of said haptic portion and said lens portion.

34. A method for making an intraocular implant comprising a lens portion and a haptic portion each having a desired shape, said lens portion having a volume and being made of a flexible first material and said haptic portion being made of a second material that is rigid relative to said first material, said lens portion being defined by first and second surface portions and by a periphery bounded by first and second closed contours, each closed contour itself bounding one of said surface portions, the method comprising steps of:

providing a bottom mold part having a top surface with a central portion corresponding to said first surface portion bounded by said first closed contour and having a peripheral portion that is set back relative to said first closed contour;

providing a plate that is made of said second material and that has a central recess with a periphery that is bounded by said first and second closed contours, said plate having at least one anchor portion projecting into said recess;

disposing said plate facing said bottom mold part in such a manner that said first closed contour of said first surface portion faces the first closed contour of said plate;

disposing a second mold part above said plate, said second mold portion having a bottom surface with a central portion that corresponds to said second surface portion bounded by said second closed contour and having a peripheral portion that is set back from said second closed contour, in such a manner that the second closed contours of said plate and of the bottom surface of said second mold part face each other;

inserting a volume of said first material in liquid form into a space defined by at least one of said surface portions and by said recess, said volume of said first material being not less than the volume of said lens portion;

applying said mold parts with pressure on either side of said plate in such a manner that said first and second closed contours come respectively into mutual contact and said first material fills all of a cavity bounded by said recess and said surface portions, said cavity corresponding to the desired shape of said lens portion, any excess of said first material being expelled from said cavity;

solidifying said first material to bring said first material to a stable final state having a shape corresponding to the desired shape of said lens portion, said anchor portion forming an insert inside said lens portion;

unmolding said plate and said first material; and machining said plate to achieve a desired shape for said haptic portion.

* * * * *